US00PP17317P2

(12) United States Plant Patent
Austin

(10) Patent No.: US PP17,317 P2
(45) Date of Patent: Dec. 26, 2006

(54) SHRUB ROSE PLANT NAMED 'AUSNEIL'

(50) Latin Name: *Rosa hybrida*
Varietal Denomination: AUSneil

(75) Inventor: David C. H. Austin, Albrighton (GB)

(73) Assignee: David Austin Roses Limited, Wolverhampton (GB)

( * ) Notice: Subject to any disclaimer, the term of this patent is extended or adjusted under 35 U.S.C. 154(b) by 0 days.

(21) Appl. No.: 11/048,481

(22) Filed: Jan. 31, 2005

(51) Int. Cl.
*A01H 5/00* (2006.01)

(52) U.S. Cl. ..... Plt./103

(58) Field of Classification Search ..... Plt./103, Plt./102, 107, 133, 137, 144, 148
See application file for complete search history.

(56) References Cited

U.S. PATENT DOCUMENTS

PP8,765 P * 6/1994 Austin ..... Plt./103

* cited by examiner

*Primary Examiner*—Howard J. Locker
(74) *Attorney, Agent, or Firm*—Klarquist Sparkman LLP

(57) ABSTRACT

Shrub rose plant suitable for cut flower production in greenhouse conditions having upright growth and white blooms with a hint of pink blush and strong myrrh fragrance.

1 Drawing Sheet

Genus and species: *Rosa hybrida.*
Variety denomination: 'AUSneil'.

ORIGIN OF THE INVENTION

The present invention relates to a new and distinct variety of a shrub rose plant named 'AUSneil' which was originated by me by crossing an unnamed, unpatented seedling with an unnamed, unpatented seedling.

BACKGROUND OF THE INVENTION

The primary objective of this breeding was to produce a shrub rose plant suitable for year round cut flower production under standard greenhouse conditions having white blooms with a hint of blush, a strong myrrh fragrance and a long vase life, produced on strong, upright stems.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. White blooms with a pink blush.
2. Upright growth.
3. Strong myrrh fragrance.
4. Suitable for cut flower production under greenhouse conditions.

Asexual reproduction of this new variety by budding, as performed at Albrighton, England, shows that the foregoing and all other characteristics and distinctions come true to form and are established and transmitted through succeeding propagations.

Comparison with Parents

'AUSneil' has white blooms touched with a blush of pink and a strong myrrh fragrance which differs from the white blooms with no fragrance of the pollen parent and the pale pink blooms borne in small clusters of the seed parent.

Comparison with Similar Variety

'AUSlevel' (U.S. Plant Pat. No. 8,765) has a greater number of petals and is creamy white.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where oridnary dictionary significance of color is indicated.

Parentage:
*Seed parent.*—Unnamed Seedling (Unpatented).
*Pollen parent.*—Unnamed Seedling. (Unpatented).

FLOWER

Observations made from plants commencing at two years of age grown in a greenhouse environment at Albrighton, England.

Blooming habit: Continuous.
Bud:
*Size.*—About 3 cm long and 1.5 cm in diameter when the petals start to unfurl.
*Form.*—The bud form is pointed ovoid.

*Color.*—When sepals first divide, bud color is Red Group 36B. When half blown, the upper sides of the petals are Yellow-White Group 158B with a tint of Red Group 38B; and the lower sides of the petals are Green-White Group 157A.

*Sepals.*—Color: Upper surface: Green Group 137C with shade of Greyed-Orange Group 176A in center. Lower surface: Green Group 139C. Length: 4.7 cm. Width: 0.8 cm. Shape: Subulate. Surface texture: Upper surface: Smooth. Lower surface: Pubescent. There are three heavily appendaged sepals. There are two unappendaged sepals with glandular edges.

*Receptacle.*—Color: Yellow-Green Group 144A. Shape: Funnel. Size: Medium, about 1.2 cm long×1 cm wide. Surface: Smooth.

*Peduncle.*—Length: Long, averaging about 8.5 cm. Surface: Smooth. Color: Yellow-Green Group 144A. Strength: Strong.

Bloom:

*Size.*—Large. Average open diameter is about 12 cm.

*Borne.*—In corymb-shaped clusters of two to three blooms. For cut flower production, buds may be nipped out to leave a single bloom.

*Flowering stems.*—Strength: Normal. Average length is about 80 cm with a diameter of 5 mm. Number: 20–22.

*Form.*—When first open: Cupped. Permanence: Outer petal edges curl back.

*Petalage.*—Number of petals under normal conditions: 86.

*Color.*—The upper sides of the petals are White Group 155D with a pink blush. The reverse sides of the petals are White Group 155D with a pink blush. The bases of the petals are Yellow Group 5D. The major color on the upper sides is White Group 155D.

*Variegations.*—None.

*Discoloration.*—The general tonality at the end of the first day: White Group 155D. At the end of the third day: White Group 155D.

*Fragrance.*—Strong, myrrh.

Petals:

*Texture.*—Satiny.

*Size.*—Width: 5.5 cm. Length: 6.8 cm.

*Surface.*—Smooth.

*Shape.*—Obdeltoid. Margin: Notched and reflexing with weak undulation. Apex Shape: Cuspidate. Base Shape: Pointed. Form: Incurved, upper third is recurved.

*Arrangement.*—Informal.

*Petaloids.*—None.

*Persistence.*—Petals hang on and dry.

*Lastingness.*—On the plant: Long (about 6–8 days). As a cut flower: Long (about 6–8 days).

Reproductive parts:

*Stamens.*—Number: 25. Length: 10 mm. Anthers: Length: 3 mm. Color: Yellow-Orange Group 22A. Arrangement: Regular around styles. Filaments: Color: Yellow Group 13A. Length: 7 mm. Pollen: Color: Yellow-Orange Group 22A.

*Pistils.*—Number: 55. Length: 9 mm. Styles: Color: Yellow Group 2D and Red Group 48C at base. Length: 8 mm. Stigmas: Color: Yellow Group 9C. Length: 1 mm.

*Hips.*—None observed.

PLANT

*Form.*—Shrub.

*Growth.*—Vigorous, upright, bushy.

*Age at maturity.*—One and one-half years.

*Mature plant.*—Height: 1 m. Width: 0.5 m.

*Rootstock.*—*Rosa multiflora inermis* for the observed plants in the United Kingdom.

Foliage: Number of leaflets on normal mid-stem leaves: Usually 3 and occasionally 5 including terminal leaflet.

*Size.*—Medium. About 12.3 cm long×11.3 cm wide.

*Quantity.*—Normal. Average number leaves per flowering stem: 9.

*Color.*—New foliage: Upper side: Green Group 137A. Lower side: Greyed-Red Group 178A. Old foliage: Upper side: Green Group 139A. Lower side: Yellow-Green Group 146B with a tint of Greyed-Orange Group 176B.

Leaflets:

*Size.*—About 7 cm long×4.5 cm wide.

*Shape.*—Pointed oval.

*Base shape.*—Obtuse.

*Apex shape.*—Acuminate.

*Texture.*—Leathery.

*Edge.*—Serrated.

*Serrations.*—Double.

*Upper surface.*—Matte.

*Petiole.*—Color: Greyed-Orange Group 176B.

*Petiole rachis.*—Color: Greyed-Orange Group 176B. Underside: With prickles.

*Stipules.*—Length: 1.7 cm, bearded.

*Auricle shape.*—Subulate.

*Disease resistance.*—Resistant to mildew, blackspot and rust under greenhouse growing conditions with average day temperature maintained at 17.5 degrees C.

*Pest resistance.*—Not tested.

*Vein color.*—Yellow-Green Group 144D.

*Venation pattern.*—Reticulate.

Wood:

*New wood.*—Color: Green Group 138A. Bark: Smooth.

*Old wood.*—Color: Green Group 137B. Bark: Smooth.

*Internode distance.*—5.5 cm.

Prickles:

*Quantity.*—On main canes from base: Usually none, occasionally a few. On laterals from main canes: Ordinary, 12 per 30 cm per stem length.

*Form.*—Straight.

*Length.*—9 mm.

*Color when young.*—Red Group 39B with Yellow-Green Group 151C at base.

*Color when mature.*—Grey-Brown Group 199B.

Small prickles:

*Quantity.*—On main stalks: Few. Number per stem length: 8 per 5 cm. On laterals: Confined to a dense cluster (7–20 per 5 cm length) at bottom of stem. None on balance of stem.

*Color.*—When young: Red Group 39B with Yellow-Green Group 151C at base. When mature: Grey-Brown Group 199B.

Winter hardiness: Not tested.

I claim:

1. A new and distinct variety of rose plant of the shrub class suitable for cut flower production in greenhouse conditions, substantially as herein shown and described, characterized particularly by its upright growth and white blooms with a hint of pink blush and strong myrrh fragrance.

* * * * *

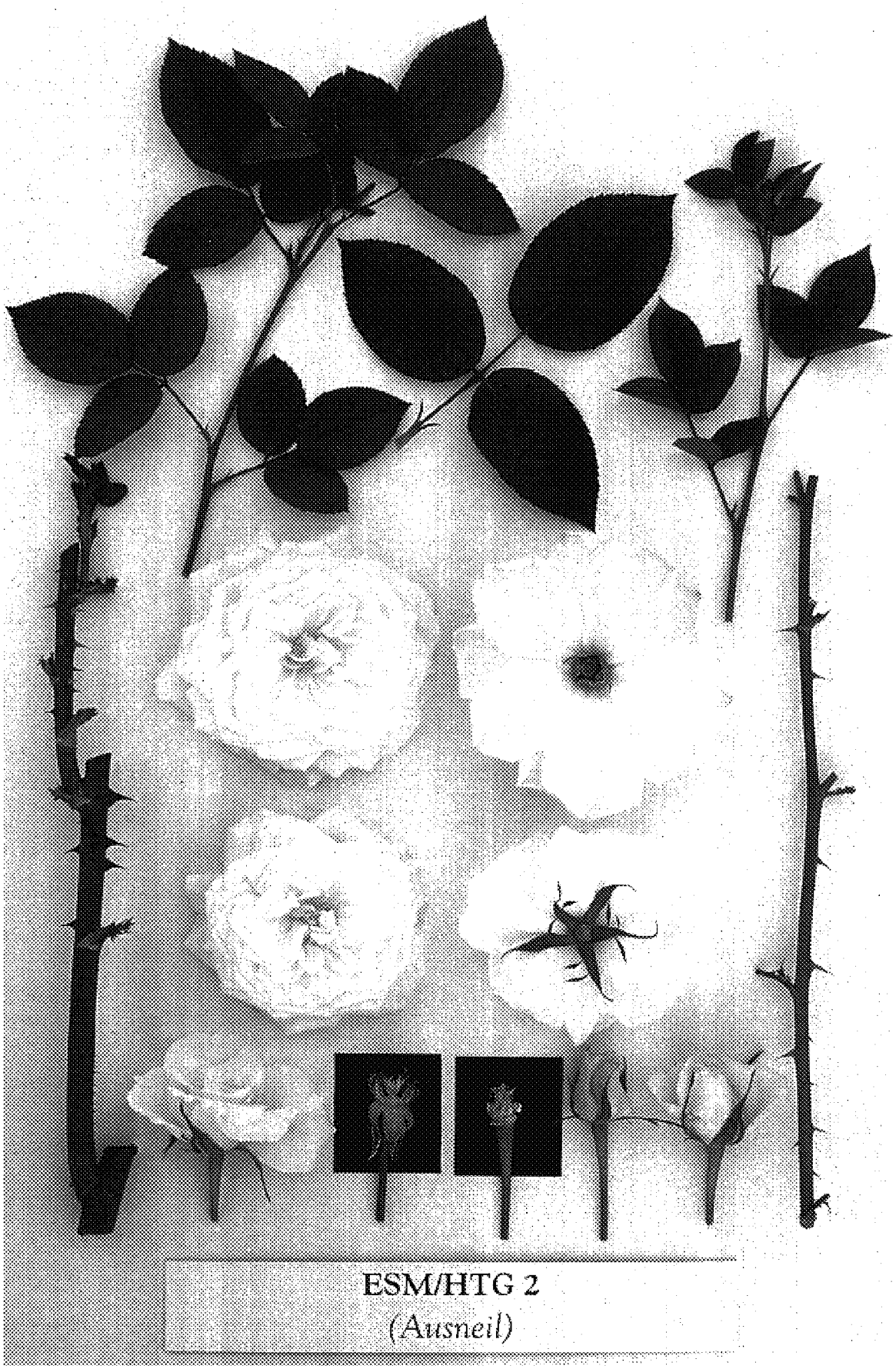
ESM/HTG 2
*(Ausneil)*